United States Patent [19]
Schwartz et al.

[11] Patent Number: 6,159,070
[45] Date of Patent: Dec. 12, 2000

[54] MATERNITY GARMENT

[76] Inventors: Rivka Devorah Schwartz, One Joshua Ct., Monsey, N.Y. 10952; Gitty Ziegler, Nine Stetner, Spring Valley, N.Y. 10977-2507

[21] Appl. No.: 09/492,367

[22] Filed: Jan. 27, 2000

[51] Int. Cl.[7] .................................................. A41C 1/08
[52] U.S. Cl. .............................. 450/155; 450/100; 2/406
[58] Field of Search ..................... 450/155, 94, 95, 450/97, 100, 101, 102, 103, 104, 105, 106, 107–109; 2/400–408; 604/385.1, 391, 392, 394, 397

[56] References Cited

U.S. PATENT DOCUMENTS

| | | | |
|---|---|---|---|
| 1,076,287 | 10/1913 | husar | 450/155 |
| 1,185,672 | 6/1916 | Huettner | 450/155 |
| 2,584,279 | 2/1952 | McDowell | 450/155 |
| 3,454,003 | 7/1969 | Sailhen | 450/155 |
| 4,789,372 | 12/1988 | Wicks | 450/155 |
| 5,928,059 | 7/1999 | Wicks | 450/155 |

*Primary Examiner*—Gloria M. Hale
*Attorney, Agent, or Firm*—Myron Amer PC

[57] ABSTRACT

In the providing of abdominal support to a pregnant mother-to-be in the latter months of gestation in which her protruding semi-spherical abdominal shape is used to advantage to hold in place criss-crossing straps which supply the support, wherein the upper ends of the straps are attached to a closed loop elastic band which is positioned above, and therefore is prevented from slipping out of position, by the protruding semi-spherical abdominal shape.

1 Claim, 1 Drawing Sheet

U.S. Patent  Dec. 12, 2000  6,159,070
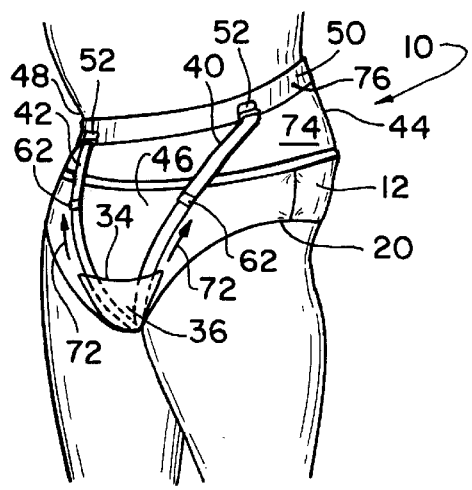
FIG.2
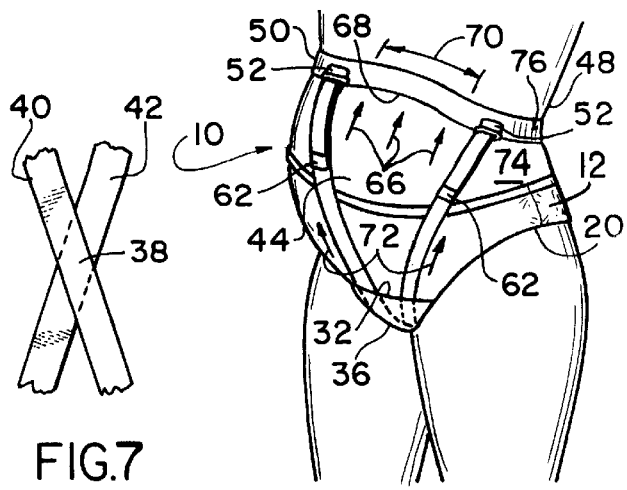
FIG.7
FIG.1
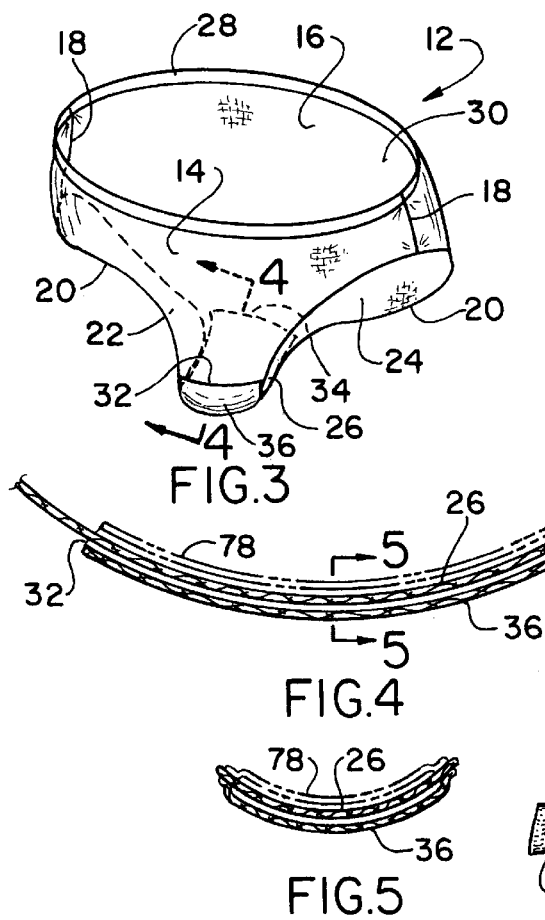
FIG.3
FIG.4
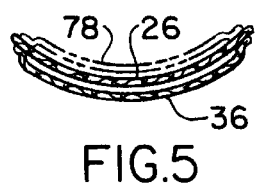
FIG.5
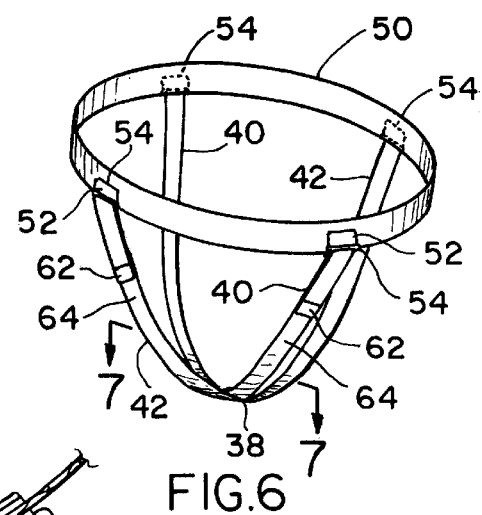
FIG.6
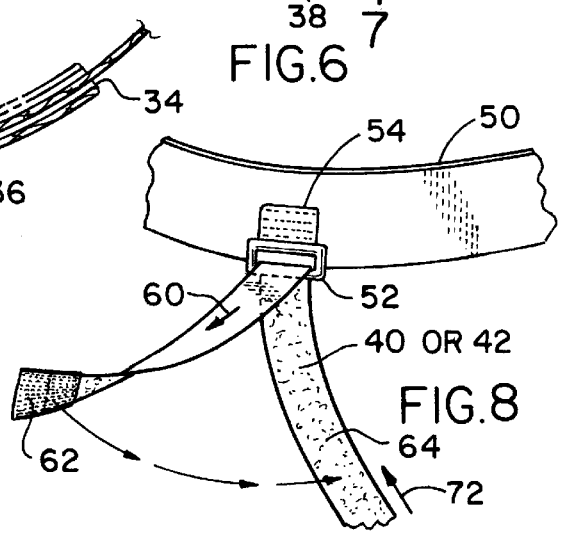
FIG.8

MATERNITY GARMENT

The present invention relates Generally to an improved maternity garment of a type providing abdominal support during the latter months of a nine-month gestation period of an impending birth, the improvements more particularly using to advantage the gestation-produced forwardly protruding semi-spherical abdominal shape to facilitate the extent of abdominal support that is provided, all as will be better understood as the description proceeds.

EXAMPLE OF THE PRIOR ART

Lower torso maternity garments for medical reasons, i.e., to provide compression therapy for vulvar varicosities during pregnancy, as one exemplary end use, are well known in the patented literature, one such patent being U.S. Pat. No. 5,217,403 for "Maternity Support Undergarment" issued to Vestal L. Nobbes on Jun. 8, 1993. The garment of the '403 patent, as well as the garments of all other known patents, has an abdominal support panel attached to extend upwardly from the crotch of a panty and straps connected from the upper edge of the abdominal support panel to sites of attachment on the rear of the panty. While generally useful for the purposes intended, the position of the abdominal support panel against the lower portion of the gestation produced semi-spherical abdominal shape is held against release or slippage only by the extent of tautness of the straps. In practice, it has been found that this contributes to discomfort in that the straps are pulled tighter than they have to be.

Broadly, it is an object of the present invention to provide a lower torso maternity garment overcoming the foregoing and other shortcomings of the prior art.

More particularly, it is an object to achieve compression in the crotch area of the garment using pressure-applying straps connected to a closed loop band that is advantageously positioned above the gestation-produced semi-spherical abdominal shape so that the noted shape is in an interposed position between the band and crotch area to thereby contribute to minimizing descending slippage movement of the band and inadvertent release or lessening of the abdominal support being provided.

The description of the invention which follows, together with the accompanying drawings should not be construed as limiting the invention to the example shown and described, because those skilled in the art to which this invention appertains will be able to devise other forms thereof within the ambit of the appended claims.

FIG. 1 is a perspective front view, as seen from the left side, of the maternity garment in use;

FIG. 2 is a perspective rear view, as seen from the right side, of the maternity garment in use;

FIG. 3 is an isolated perspective view of the panty component;

FIG. 4 is a cross sectional view taken along line 4—4 of FIG. 3;

FIG. 5 is a cross sectional view taken along line 5—5 of FIG. 4;

FIG. 6 is an isolated perspective view of the criss-cross strap component;

FIG. 7 is a detail view of the criss-cross strap component of FIG. 6 taken along line 7—7 of FIG. 6; and;

FIG. 8 is a detail perspective view of a buckle component.

As is well known by common experience, during the nine-month gestation of a birth, the latter months form a forwardly protruding semi-spherical abdominal shape for which typically an expectant mother requires a maternity garment providing abdominal support for comfort and also for medical reasons, i.e., to provide compression therapy for vulvar varicosities during pregnancy, and to minimize perineal edema following abdominal liposuction or other surgical procedure. Method aspects of the invention propose a maternity garment, generally designated 10 in the wearing use of which applying the supporting force is facilitated by being imparted in two stages and in which the gestation-produced abdominal shape is used to advantage to maintain the application of the supporting force.

A component used in the practice of the method applying abdominal support according to the present invention is a panty 12 of stretch fabric construction material having a front panel 14, and back panel 16 joined together at either one and a second side seam 18 providing edges 20 bounding left and right leg openings 22, 24, and a crotch 26 interconnecting the front and rear panels 14, 16 and located between adjacent length portions of the leg-opening bounding edges 20. Completing construction of the panty 12 per se is typically a decorative band 28 stitched about an upper waist opening 30 of the panty.

For its abdominal-supporting function, panty 12 is provided with an opposite open-ended, as at 32 and 34, fabric sleeve 36 stitched or otherwise appropriately attached in overlying relation to the crotch 26.

Two straps in a crisscross pattern, as best illustrated in FIG. 6, are threaded through the sleeve 36 so that the intersection site 38 of the straps 40, 42 is within the sleeve 36 in the vicinity of the crotch 26 and thus of the vagina, and from said intersecting site 38 the strap length portions exit in a v-shape, wherein the v-shape in front bounds therebetween the protruding semi-spherical abdominal shape 44 and the v-shape in back the user's buttock area 46, which typically anatomically is an expanse in shape exceeding the shape of the user's waist 48.

The exiting v-shapes of the free ends of the straps 40 and 42 are maintained in this orientation by connection to a closed loop band 50 of stretch fabric construction material having four buckle means, individually and collectively designated 52, in circumferentially spaced locations 54 about the band 50 which dictates that each exiting strap free end 56 subtend a 45 degree angle to the horizontal.

In wearing the maternity garment 10, the user is instructed to position the panty 12 with the criss-crossing straps 40, 42 as a lower torso garment, and to tighten the straps 40, 42 in manually pulling them, as depicted at 60, through the buckle means 52 after which interconnecting male and female connecting patches 62 and 64 prevent inadvertently unthreading of the straps 40 and 42. The tightening of the strap 40 and 42 completes a first stage adjustment in the maternity garment 10 effective to provide abdominal support.

In accordance with the present invention a second stage adjustment is afforded by urging the central length portion of the band 50 in ascending movement 66 so it makes contact, as at 68, above the gestation-produced abdominal shape 44. Consequently the gestation-produced abdominal shape contributes to blocking descending slippage of the band length portion 70 as might diminish the extent of the forces 72 supporting the abdomen 44 and applied, for medical reasons, in the crotch area 26.

In practice it has been found that the anatomical size differences in girth between the waist 48 and the buttock 46, and particularly the hips 74, contributes to maintaining the side length portions 76 of the band 50 by blocking in similar fashion to that already described any slippage of the band length portions 76 below the waist 48.

Also, although not shown, a second, inner equivalent of the positioning sleeve 36 is contemplated being sewn over the inside surface of the crotch 26. This provides the user with an option of use in which the straps 40, 42 are masked from view beneath the panty 12 which is thought by some to present a more desirable appearance.

While the apparatus for practicing the within inventive method, as well as said method herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

What is claimed is:

1. In providing abdominal support to a pregnant female during which progressing gestation forms a forwardly protruding semi-spherical abdominal shape, a method facilitating the extent of abdominal support provided consisting of the steps of:

a) using a panty of stretch fabric construction material of a type having a front panel, a rear panel, edges bounding left and right leg openings, and a crotch connecting said front and rear panel and located between length portions of leg opening adjacent edges;

b) attaching an opposite open-ended positioning sleeve over said crotch;

c) threading two straps to impart a criss-cross orientation to each other through said positioning sleeve such that said straps are in superposed crossing relation within said sleeve at said crotch and exit from said opposite end openings of said sleeve in v-shapes bounding therebetween said protruding semi-spherical abdominal shape covered by said front panel and a buttocks shape covered by said rear panel;

d) providing a closed loop waist band of stretch fabric construction material having four buckle means circumferentially spaced thereabout for receiving in threaded relation therethrough a cooperating free end of said v-shape oriented straps;

e) manually tightening said straps by pulling movement thereof through said buckle means to exert a preliminary supporting force applied in said crotch vicinity; and f) urging a medial front length portion of said waist band in ascending movement above said protruding semi-spherical abdominal shape to exert a supplementing supporting force applied in said crotch vicinity;

whereby said medial front length portion of said waistband is prevented from slipping from said raised position thereof by said gestation-produced abdominal shape as might diminish said applied supporting force.

* * * * *